United States Patent [19]

Moteni

[11] Patent Number: 4,985,907
[45] Date of Patent: Jan. 15, 1991

[54] DENTAL X-RAY APPARATUS FOR PANORAMIC TOMOGRAPHY

[75] Inventor: Roberto Moteni, Milan, Italy

[73] Assignee: U.S. Philips Corporation, New York, N.Y.

[21] Appl. No.: 347,315

[22] Filed: May 3, 1989

[30] Foreign Application Priority Data

May 6, 1988 [EP] European Pat. Off. ........ 88200900.4

[51] Int. Cl.5 ............................. A61B 6/02; A61B 6/14
[52] U.S. Cl. ....................................... 378/139; 378/38; 378/40; 378/11
[58] Field of Search ........................ 378/39, 38, 11, 40, 378/196

[56] References Cited

U.S. PATENT DOCUMENTS

| | | | |
|---|---|---|---|
| 4,039,839 | 8/1977 | Ohta et al. | |
| 4,241,254 | 12/1980 | Välilä | 378/40 |
| 4,418,419 | 11/1983 | Schreiber et al. | 378/95 |
| 4,661,967 | 4/1987 | Nishikawa | 378/40 |
| 4,783,793 | 11/1989 | Virta et al. | 378/39 |
| 4,856,038 | 8/1989 | Guenther et al. | 378/39 |

FOREIGN PATENT DOCUMENTS

| | | |
|---|---|---|
| 0035307 | 2/1981 | European Pat. Off. . |
| 0215757 | 2/1986 | European Pat. Off. . |
| 2186770 | 8/1987 | Fed. Rep. of Germany . |

Primary Examiner—Janice A. Howell
Assistant Examiner—Don Wong

[57] ABSTRACT

Dental X-ray apparatus for panoramic tomography in which an X-ray source and X-ray detection means are carried by a moving mechanism for panoramic imaging movements including translation and rotation of the X-ray source and of the detection means with respect to an object to be examined. The panoramic movements are controlled by data momentally supplied from a microcomputer for two individual translation movements in a plane and for rotation movement about an axis perpendicular to that plane.

12 Claims, 2 Drawing Sheets

DENTAL X-RAY APPARATUS FOR PANORAMIC TOMOGRAPHY

BACKGROUND OF THE INVENTION

1. Field of the Invention

The present invention relates to an X-ray apparatus for panoramic tomography comprising an X-ray source and X-ray detection means and provided with a moving mechanism for controlling movements for panoramic imaging, including translation and rotation of the X-ray source and of the detection means with respect to an object to be examined.

2. Description of the Prior Art

In known panoramic X-ray apparatus for dental photography the X-ray beam is turned around the patient's head in such a way that the dental arch becomes photographed as a flat picture on a moving film.

In order to get a sharp picture of the object and to make structures in front of the object and behind it invisible by "fogging" out of focus, the transverse velocity of the film with respect to the ray beam is kept equal to the sweep velocity of the ray beam in the object taking in consideration the magnification ratio. The magnification is determined by the ratio of the distance between the focus and the film to the distance between the focus and the object.

The thickness of the layer being photographed sharply is directly proportional to the distance of the the instantaneous center of rotation from the object plane, and inversely proportional to the magnification and to the width of the ray beam. From a point of view of how the object will be represented it is important only how the X-ray, focuses and how the object and the film plane are mutually registered.

In order to realise an orthogonal radiogram of the teeth and the jaw, typical to panoramic tomography X-ray equipment, a thin X-ray beam is generated by penetrating the relevant parts of a patient. The anode current and the anode voltage of an X-ray source are controlled according to the properties of the patient while the X-ray beam is rotated around the patient along a path such that the X-ray beam meets the jaw and the teeth as perpendicularly as possible. To this end, the centre of rotation of the X-ray beam is usually translated during X-ray emission, either into a limited number of of fixed positions or continuously along an adapted path. This translation is usually achieved by means of a cam or equivalent mechanism. This implies that three different kinematic axes are involved in the movement of the X-ray beam to wit: the angle of rotation and the two cartesians X and Y of the centre of rotation. A film and a film cartridge, located on the opposite side of the patient with respect to an X-ray tube, are moved with such a speed that a desired layer of the patient's chinbone and dental system are represented on the film sharply.

It is also known to use a separate motor for the film cartridge motion; usually this motor is of constant-speed type, and the gear ratio of the film cartridge is mechanically changed by means of forced control provided by the rotary movement.

A drawback of known control systems based on mechanically interconnected motion speeds is that the ratio of the motion speeds is mechanically fixed and cannot be changed in the different stages of the exposure; therefore only one type of jaw profile can be photographed sharply with these devices. As known, human jaws vary, and therefore it has been necessary to make compromises in the known devices, for example such that a so called average jaw profile in the photographed sharp layer in order to have different jaws be photographed at least satisfactorily.

For eliminating these drawbacks a separate film cartridge transport motor is provided in a further known embodiment, the speed of which can varied as before with control provided by the rotary motion but also separately so that the layer being photographed sharply can when desired be changed within certain limits thus aiming at getting as good panoramic photograph as possible of each jaw shape.

In the last-mentioned known equipment, in which the rotary motion and the film cartridge movement have their own motors, the rotary motion motor is a constant-speed motor; in consequence it has been possible to change the layer being photographed sharply only by changing the speed of the film cartridge. This procedure has the inevitable consequence that the exposing time will change directly proportionally to the film cartridge transport speed, and the picture will not be evenly exposed; instead, it will have lighter and darker stripes depending on to what direction the sharply-represented layer has been corrected with respect to the basic shape determined by the mechanical system. Similarly, in these known systems with two separate motors it has not been possible to make the necessary correction in order to compensate the absorption of radiation caused by the cervical spine, because always at least one of the motors is of the constant-speed type. Therefore a compensation is introduced by changing the intensity of the X-ray beam, but as a milli-ampere-regulation with which the intensity is controlled is too slow due to properties of the glow filament of the X-ray tube, one must change the intensity by changing the anode voltage of the X-ray tube. Depending on the properties of the patient and intensifying screens used, the maximum appropriate contrast is achieved with a certain anode voltage; deviating from this voltage results in worse contrast. Therefore in an apparatus as disclosed in EP No. 215757 a control system is introduced on the basis of control data and program stored into it, arranged to control both the speed of a rotary motion motor of an arm and the speed of a film transport motor and the distribution of these speeds during an exposure sequence independently of each other in order to obtain sharp images with suitable exposing time photograph dental systems of varying sizes and shapes with a panoramic device. The use of a mechanically fixed movement by the motor drive of the arm still restricts an exact panoramic imaging.

SUMMARY OF THE INVENTION

In order to avoid this limitation a panoramic apparatus according to the invention is characterized in that all movements are individually motor driven the movements being controlled by data supplied by a microcomputer.

Due to the fact that all movements in the apparatus are individually motor-driven no restrictions occur for following the most appropriate curve for imaging. It is remarked that a motor driven apparatus per se is known from U.S. Pat. No. 4,418,419 but there use is made of information initiated by patient byting which of course always includes a risk of discomfort for the patient and can not be used with toothless patients. In addition, the curve depicted in focus by an apparatus according to the invention corresponds to contour of the occlusal plane that is at the biting line of the teeth. Actually in dental panoramic radiography there is the need to depict the contour a the teeth roots plane, this contour being different from the one at the occlusal plane due to root inclination. The control system as described in U.S. Pat. No. 4,418,419 is, however, applicable for the apparatus according to the present invention.

In a preferred embodiment the control system is structured to control positions of moving parts momentally and continuously by imparting pre-determined moving steps of motor-drives. With such a control system any curve for imaging can be followed without the use of a mechanical cam follower or the like.

The drive-motors are preferably stepping motors such that digital data directly can be used for the control thereof without need for signal conversion or any position feedback to regulate movements. Alternatively DC-motors provided with encoding systems can be used which potentially a higher reliability of movement control.

BRIEF DESCRIPTION OF THE DRAWING

The invention will now be described in detail with reference to the drawing in which some embodiments are illustrated. In the drawings.

DETAILED DESCRIPTION OF THE PREFERRED EMBODIMENTS

Figure 1:
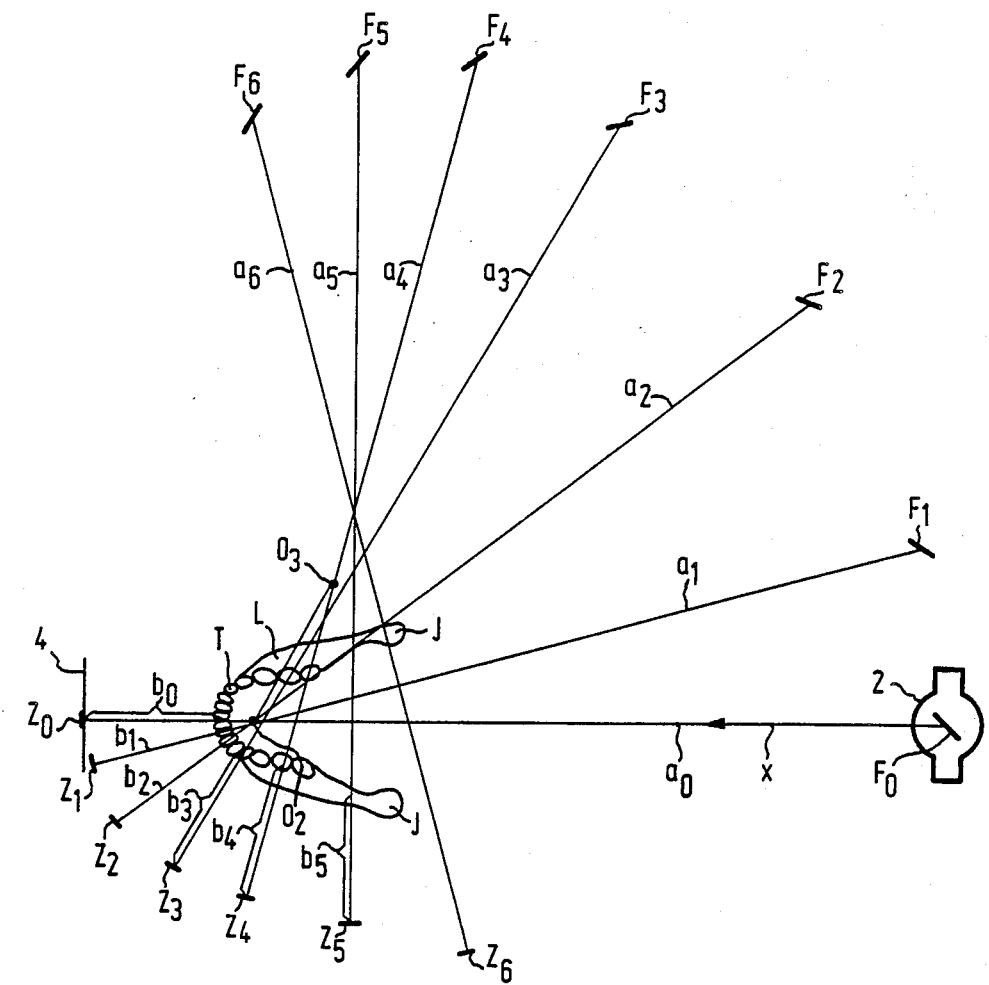
FIG. 1 shows a plan view of ray projections corresponding to several successive positions of X-ray source and detecting means which can be accomplished with a control system in accordance with the invention.

FIG. 1 illustrates a photographing geometry and projection accomplished with the apparatus in accordance with the invention and shows an X-ray tube 2 with a focus F. Seven different successive positions of the X-ray tube are indicated with references $F_0$ to $F_6$. The X-ray tube 2 transmits an X-ray beam X through teeth T and through a jawbone L onto a film 4 along a line a. The passage of the X-ray from starting position $F_0$ to $F_6$ also is shown by seven respective different central rays $a_0$ to $a_6$, ending at respective positions $Z_0$ through $Z_6$ for the film 4. Joints of the jawbone L are marked with J.

In a front area of a dental arch, represented by the region between the rays $a_0$ and $a_1$, an arm (such as arm 10 in FIG. 2) carrying the X-ray tube 2 on its one end and the filmsheet 4 on its other end, rotates in a horizontal plane around a vertical axis $O_2$. In the region between the rays $a_2$ and $a_4$ the center of rotation normally smoothly moves along a curved path to the vertical axis $O_3$, after which the vertical axis further draws away from the ray $a_0$ corresponding to the center axis of the apparatus of the invention. With this geometry the orthogonality of the representation be comes true with good accuracy in the front dental arch area, in the side areas and also in the rear part of the jawbone L up to the joints J. Magnification should also be constant in the whole image field; this is proved by for instance the fact that the distance $b_0$ to $b_5$ of the film from the photographed layer should be constant over the whole path.

If the distance $b_0$ to $b_5$ is constant, it should be possible to bring the film 4 closer to a patient in order to reduce the magnification ratio without a risk of the film cartridge hitting the patient. This being one of the features of an apparatus according to the invention.

Figure 2:
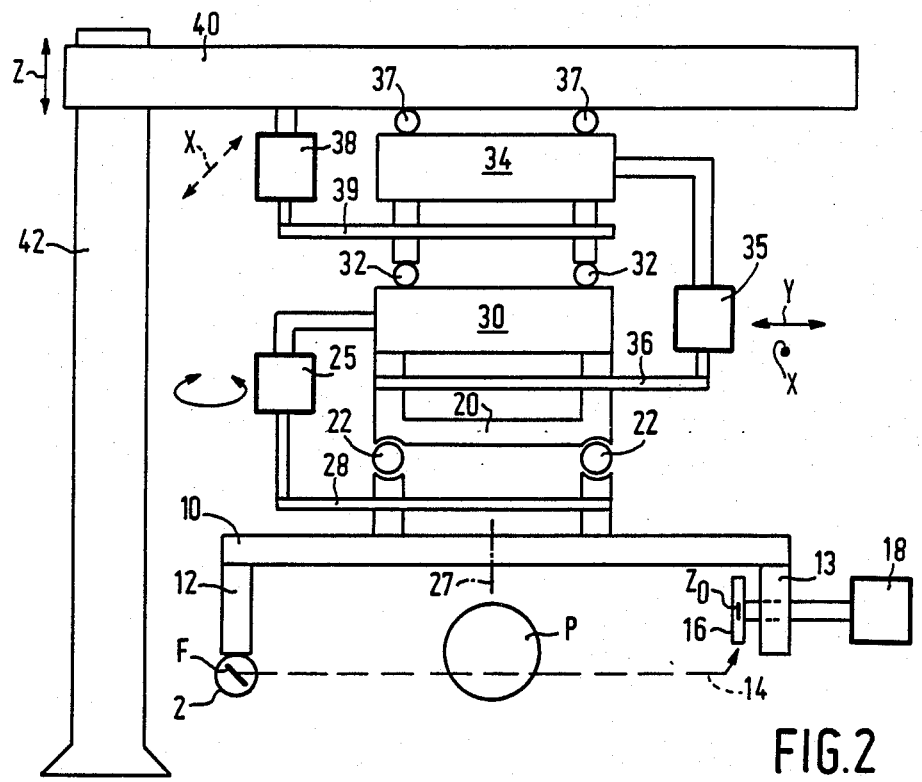
FIG. 2 shows a central vertical section of an apparatus provided with individual motor-drives and a control system in accordance with the invention and, FIG. 3 is a block diagram of a control system in accordance with the invention.

FIG. 2 shows schematically a mechanism for panoramic movements according to the invention. An arm 10 carries a support 12 for the X-ray tube 2 with the focus F on one side and a support 13 for X-ray detection means 14 on an opposite side. The X-ray detection means are illustrated as a filmsheet registered in a film cartridge 16 provided with a drive motor 18 for cartridge transport. The arm 10 is suspended from a carriage 20 for example by means of a circular bearing 22. The carriage 20 is connected to a drive motor 25 by way of a belt 28 enabling rotation of the arm 10 around an axis 27 which axis, as will be elucidated further on, has a movable position with respect to a patient P to be examined.

The drive motor 25 is fixed to a carriage 30 which is suspended via a linear bearing 32 from a further carriage 34 such that carriage 30 together with the drive motor 25 can execute a linear movement denoted as Y-direction with respect to carriage 34, by way of a belt 36 which is driven by a motor 35 fixedly mounted to carriage 34.

In a similar manner the carriage 34 is suspended with the aid of a bearing mechanism 37 in order to enable a linear movement in an X-direction of the carriage 34 with respect to a supporting arm 40. For this movement the carriage 34 is coupled with a belt 39 to a drive motor 38 which is fixedly mounted to the supporting arm 40. The supporting arm 40 is slidably suspended to a column 42 such that the arm 10 with the X-ray 2 tube and the detection means 14 can translated in a vertical direction perpendicular to the X- and Y-direction for positioning the imaging system to the height of a patient P. The column 42 forms the fixed part of the apparatus. The moving parts of the mechanism are coupled by vibration free couplings.

Figure 3:
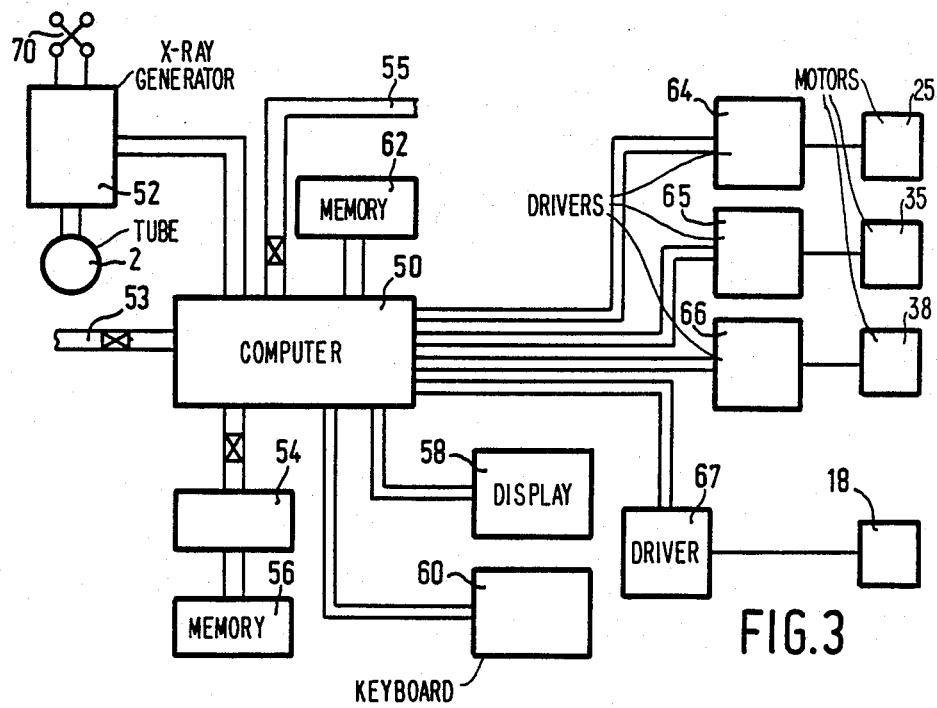

FIG. 3 shows a scheme for a control system for an apparatus according to the invention. The scheme shows a microcomputer 50 can be split up in different microprocessors on different circuit boards if appropriate for a rational architecture of various operative tasks of the equipment. To the microcomputer 50 an X-ray generator 52, preferably of a high frequency converter type, for the X-ray tube 2, eventually an external communication line 53 for linking the system to a stand alone computer system, and a connection bus 55 to the system are coupled, as well as a non erasable memory 56, a display 58, for example an alphanumeric gas discharge display, and a keyboard 60. The non erasable memories can either be combined in one single integrated circuit, different logical areas of the memory being allocated to operative programme software and to the data tables, or different peaces of integrated circuits can be used for operative software and or data tables. To the microcomputer 50 a further memory 62 preferably an electrical programmable read only memory is added containing operating software and kinematic profile data. From the software and the data tables signals can be derived for a direct activation of drivers 64 through 67 for the motors 25, 35, 38 and 18 respectively. The X-ray generator 52 is linked to a power main 70, and, as well, control signals such as diagnostic signals, digital or analogic, can act between the microcomputer 50 and the X-ray generator 52. The bus 55 collects signals from various on/off sensors in the system such as reset microswtiches, range microswitches, film cassette sequence switches, and for selection of X-ray tube heads and collimator positions (e.g. for selecting orthoralix or cephalographic exposures). The motors 18, 25 and 38 provide the respective support 10 and carriages 30 and 34 separate, independent respective rotation about axis 27 and translation movements in directions y and x in a plane. The translation movement of support 10 is in two individual respective directions y and x in accordance with the displacements of the respective carriages 30 and 34.

What is claimed is:

1. X-ray apparatus for panoramic tomography of an object to be examined comprising an X-ray source and X-ray detection means and a moving mechanism for translation and rotation of the X-ray source and of the X-ray detection means with respect to the object to be examined, characterized in that the moving mechanism is controlled by data momentally supplied from a microcomputer for two separate, independent directions of translation movement in a plane and for separate, independent rotation movement about an axis perpendicular to that plane whereby each said movement is made independently of the other movements, said moving mechanism being arranged so that said rotation movement axis is displaceable in said two individual directions.

2. X-ray apparatus as claimed in claim 1, characterized in that said moving mechanism comprises a motor driven movement means for the X-ray detection means individually controlled by data momentally delivered by the microcomputer.

3. X-ray apparatus as claimed in claim 1, characterized in that the moving mechanism follows position profiles as controlled by data from the microcomputer in which said X-ray detection means is positionable at a range of X- and Y-positions and every angle orientation of a line directed between said X-ray source and said X-ray detection means is achievable.

4. X-ray apparatus as claimed in claim 3, characterized in that the moving mechanism comprises a supporting arm for the X-ray source and the X-ray detection means coupled with a frame of the apparatus by vibration free couplings.

5. X-ray apparatus as claimed in claim 3, wherein said two directions of translation movement are X- and Y- and characterized in that the moving mechanism comprises a supporting arm for the X-ray source and X-ray detection means, and motors for X- and Y-translation movement and for rotation movement of said supporting arm are coupled with moving parts of said moving mechanism by means of belts.

6. X-ray apparatus as claimed in, claim 1 wherein said moving mechanism comprises an individual motor drive for each direction of translation or rotation movement and further characterized in that a control program performed by said microcomputer is structured to derive numerical data from tables stored in a digital memory for supplying control signals for individual motor-drives of the moving mechanism.

7. X-ray apparatus as claimed in claim 6, characterized in that the motor drives comprise stepping motors.

8. X-ray apparatus as claimed in claim 6, characterized in that the motor drives comprise direct-current motors provided with encoders.

9. X-ray apparatus as claimed in claim 6, characterized in that the software tables are adapted to maintain a constant distance between the X-ray detection means and the object to be examined.

10. X-ray apparatus for panoramic tomography of an object to be examined comprising:
an X-ray source and X-ray detection means;
support means for securing the source in spaced relation to the detection means for producing an image of said object located therebetween;
a support member;
first drive means secured to the support for displacement in first linear translation directions;
second drive means secured to said first drive means for displacement in second linear directions transverse the first directions in a given plane;
third drive means rotationally secured to said second drive means for rotation about an axis normal to said given plane such that the third drive means displaces in said first and second directions in response to the respective displacement of said first and second drive means;
means for securing the support means to said third drive means; and
means for independently driving each said first, second and third drive means regardless the relative stationary position of the other drive means to cause said detection means to displace about said object in a selected path.

11. The apparatus of claim 10 wherein said detection means includes film cartridge receiving means for receiving X-ray film and fourth drive means for movably securing said cartridge means to said detection means.

12. The apparatus of claim 10 wherein said first drive means includes a first motor fixedly secured to said support member and first translation means movably secured to the support member and coupled to said first motor for selectively displacing in said first directions in response to activation of said first motor, said second drive means includes a second motor fixedly secured to said first translation means and second translation means movably secured to said first translation means and coupled to said second motor for selectively displacing in said second directions in response to activation of said second motor and said third drive means includes a third motor fixedly secured to said second translation means and bearing means for rotatably securing said support means to said second translation means for rotation about said axis in response to activation of said third motor.

* * * * *